(12) United States Patent
Smith et al.

(10) Patent No.: US 8,864,720 B2
(45) Date of Patent: Oct. 21, 2014

(54) DOSE SETTING ELEMENT FOR A DRUG DELIVERY DEVICE AND DRUG DELIVERY DEVICE WITH DOSE SETTING ELEMENT

(75) Inventors: Christopher James Smith, Cheshire (GB); Timothy Giles Claughton, Cheshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 335 days.

(21) Appl. No.: 13/139,684

(22) PCT Filed: Dec. 17, 2009

(86) PCT No.: PCT/EP2009/067417
§ 371 (c)(1),
(2), (4) Date: Oct. 19, 2011

(87) PCT Pub. No.: WO2010/070050
PCT Pub. Date: Jun. 24, 2010

(65) Prior Publication Data
US 2012/0103328 A1    May 3, 2012

(30) Foreign Application Priority Data
Dec. 19, 2008   (EP) .................................... 08022158

(51) Int. Cl.
*A61M 5/00* (2006.01)
*G01F 11/02* (2006.01)
*A61M 5/20* (2006.01)
*A61M 5/315* (2006.01)

(52) U.S. Cl.
CPC ...... *G01F 11/023* (2013.01); *A61M 2005/2013* (2013.01); *A61M 5/20* (2013.01); *G01F 11/027* (2013.01); *A61M 2005/208* (2013.01); *A61M 5/31563* (2013.01); *A61M 5/3156* (2013.01); *A61M 5/31555* (2013.01); *A61M 5/3158* (2013.01)
USPC .......................................... 604/208; 604/207

(58) Field of Classification Search
USPC ............. 604/207–211, 186, 220, 230; 222/43
See application file for complete search history.

(56) References Cited

U.S. PATENT DOCUMENTS

| 5,975,355 | A | * | 11/1999 | Cecala et al. ................... 222/43 |
| 6,837,876 | B2 | * | 1/2005 | Bally et al. ................... 604/207 |
| 2004/0122368 | A1 | | 6/2004 | Langley et al. |
| 2006/0089607 | A1 | | 4/2006 | Chen |

FOREIGN PATENT DOCUMENTS

EP    1698365 A2    9/2006

OTHER PUBLICATIONS

Form PCT/IB/373, International Preliminary Report on Patentability.

* cited by examiner

*Primary Examiner* — Nicholas Lucchesi
*Assistant Examiner* — Weng Lee
(74) *Attorney, Agent, or Firm* — McDonnell Boehnen Hulbert & Berghoff LLP (57) ABSTRACT

The invention relates to a dose setting mechanism (1) for a drug delivery device (2), comprising a number of separate dose setting elements (3.1 to 3.*n*), wherein a dose volume and/or a dose number are/is set by moving at least one of the respective dose setting elements (3.1 to 3.*n*) from a stack position (I) to an initial position (II), and wherein a medicament dose volume is applied by moving at least one dose setting element (3.1 to 3.*n*) from the initial position (II) to a dispense position (III) and wherein the movement of the dose setting element (3.1 to 3.*n*) from the initial position (II) to the dispense position (III) is limited by at least a height (h) of the dose setting elements (3.1 to 3.*n*) in the initial position (II), wherein each dose setting element (3.1 to 3.*n*) comprises a plurality of bulges (B1 to Bm) on at least one surface side (S1), wherein the height (h) of each dose setting element (3.1 to 3.*n*) equals a sum of the thickness (D) of the dose setting element (3.1 to 3.*n*) and the bulge height (h1).

19 Claims, 5 Drawing Sheets

DOSE SETTING ELEMENT FOR A DRUG DELIVERY DEVICE AND DRUG DELIVERY DEVICE WITH DOSE SETTING ELEMENT

CROSS REFERENCE TO RELATED APPLICATIONS

The present application is a 35 U.S.C. 371 National Application of PCT/EP2009/067417 filed Dec. 17, 2009 and claims priority to European Patent Application No. 08022158.3, filed Dec. 19, 2008, the entire contents of which are incorporated entirely herein by reference.

TECHNICAL FIELD

The present invention relates to a dose setting mechanism form drug delivery device for setting a dose with a given amount of a medicament in a container in the drug delivery device. Furthermore, the present invention relates to a drug delivery device with such a dose setting mechanism.

BACKGROUND OF THE INVENTION

The drug delivery device usually comprises a container pre-filled with a medicament for multiple injections or inhalations with a pre-determined dose. For certain applications it may be desirable to set individual doses to be delivered. The user will know which dose is set.

Existing injection devices for administering fixed doses are typically designed in one of two forms—screw thread devices and ratcheted piston devices. Screw thread devices will typically have a tolerance chain for the displacement of a single dose that runs through several components.

An example of a device for administrating an injectable product in doses is described in U.S. Pat. No. 6,837,876 B2. The device includes a casing, a reservoir for the product, a piston, an advancing element which moves the piston a selected path length, and a dosing mechanism including a number of dosing bodies and a dosing element operable to move the dosing bodies, wherein the path length is selected by the dosing element moving at least one dosing body between the piston and the advancing element.

SUMMARY OF THE INVENTION

It is an object of the present invention to provide a solution of a simple and compact dose setting mechanism with a number of dose setting elements which allows variable dose volumes and/or variable dose numbers and an easy and improved sliding of the dose setting elements.

It is a further object of the present invention to provide a compact drug delivery device with a simple and compact dose setting mechanism which allows variable dose volumes and/or variable numbers of doses and an easy sliding of dose setting elements. Another object is to provide an easily manageable and operationally reliable drug delivery device with a pebble shape.

According to the first aspect of the invention the above objects are fulfilled by providing a dose setting mechanism for a drug delivery device, wherein the dose setting mechanism comprises a number of separate dose setting elements, wherein a dose volume and/or a dose number are/is set by moving at least one of the respective dose setting elements from a stack position to an initial position, and wherein a medicament dose volume is applied by moving at least one dose setting element from the initial position to a dispense position and wherein the movement of the dose setting element from the initial position to the dispense position is limited by at least a height in the initial position, wherein each dose setting element comprises a plurality of bulges on at least one surface side and wherein the height of each dose setting element equals a sum of the thickness of the dose setting element and the bulge height.

The advantage of the proposed dose setting or metering mechanism is that each individual dose volume is controlled by only one dimension of the dose setting elements—the total height of each dose setting element equal a sum of the thickness of the individual dose setting element and the bulge height. Therefore, such a dose setting mechanism allows setting a variable number of doses with individual variable dose volumes in a single drug delivery device in a very simple way. Different dose volumes and/or dose numbers can be modified simply by changing the height, especially the thickness of the dose setting elements and/or the number of the dose setting elements in the storage stack. Furthermore, there is a very small injection failure based on a very small tolerance of the height dimension so that a high accuracy of each dose volume is allowed. In an alternative embodiment each dose setting element is formed as a ball. The diameter of the ball is the height of the dose setting element.

A further advantage of the invention is that the bulges on at least one surface side, e.g. on the bottom surface side of the individual dose setting element, reduce the friction when the dose setting element is pushed to the side and allow for warping tolerances. In a preferred embodiment, the dose setting element comprises at least three bulges with a height which is very low, e.g. <1 mm, ca. 0.4 mm. The height of the bulges is generally small with the respect to the thickness of the dose setting element. Preferably, the height of the bulges is smaller than the thickness of the dose setting element. For easy sliding or guiding of the dose setting elements the bulges have a hemispherical shape. Furthermore, the opposing side ends of the dose setting elements are round and/or tapered to facilitate sliding of the dose setting elements.

In one embodiment of the invention the individual height of the respective dose setting elements positioned in the initial position define an applying travel for one dose. In other words: The total height of all positioned dose setting elements corresponds to the length of the total applying travel of all doses.

Accordingly, the individual height of each dose setting element defines an individual single dose volume of the medicament to be delivered. A total dose volume is defined by the total height of all dose setting elements positioned in the initial position.

In a further embodiment, the number of the respective dose setting elements positioned in the stack position defines the dose number to be separately delivered. For example, the dose setting mechanism can automatically deliver an injection regime, delivering regime or a titration regime where dose volumes are defined by the height of the dose setting elements.

In another embodiment the dose setting elements have the same height or different heights to define the same or different dose volumes of the medicament to be separately delivered. Such a structure and an arrangement of dose setting elements allows for setting increasing dose volumes or several numbers, e.g. seven, fixed doses or increased or decreased dose volumes e.g. for one week or for a day. A further advantage is that such a dose setting mechanism can provide a high degree of precision in delivery of set dose volumes and that the dose can be set at different dose volumes or quantities down to increments of 0.1 ml, 0.2 ml, 04 ml, 2.8 ml, etc with a compact reliable and repetitive design.

In a preferred embodiment, the respective dose setting element is a disc with a plurality of bulges on at least one surface side. Such structure of the dose setting element comprises a small tolerance stack controlling the accuracy of each dose. The disc can be designed in such a way as to facilitate accurate injection-moulding of the critical height or thickness dimension by designing to minimise shrinkage, warping, uneven surface, etc. Therefore, the disc is produced as a moulding component, e.g. an injection moulding component. In this way the tolerance on the height dimension, and hence on the dose delivered, will be very small.

In addition, depending on the usage of the invention, the respective dose setting elements may be moveable backwards from the dispense position via the initial position to the stack position and/or from the initial position to the stack position. This allows for a re-use of the dose setting mechanism and/or for a correction of an incorrectly set dose setting element. The re-use of the dose setting mechanism depends on the utilisation of the dose setting mechanism e.g. in a drug delivery device such in a needle or needle-free device, in an auto-injector or manually injector, in an inhalator, e.g. a nasal and buccal spray inhalator.

According to the other main aspect of the invention it is characterised by a drug delivery device for administering a product, comprising
  a dose setting mechanism according to any of the preceding claims,
  a fixed medical container pre-filled with a total volume of a medicament,
  a reciprocating piston with a piston rod positioned above a rear end of the container and moveable between a piston loading position and a piston delivery position,
  transfer means transferring at least one of the dose setting elements of the dose setting mechanism from a stack position to an initial position above the rear end of the container while the piston is positioned to the loading position, wherein each dose setting element comprises a plurality of bulges on at least one surface side, wherein the height of each dose setting element equals a sum of the thickness of the dose setting element and the bulge height.

The advantage is that the drug delivery device may be very easily held and applied to the skin and the injection may be easily prepared. The drug delivery device is simple to use in that a user can set dose numbers with a high degree of precision or in that the drug delivery device can be manufactured with a great number of different dose volumes and/or dose numbers in a very easy way by varying the number of stacked dose setting elements and/or heights of the stacked dose setting elements. Additionally, the user can alter the dose volume and/or the dose number as required by a certain treatment plan in a very easy way. Depending on the usage of the invention the individual dose volume is defined by the height of the individual dose setting element and the sequence of the stacked dose setting elements. The dose or dose sequence is defined and fixed during manufacturing of the device. Alternatively, the dose or dose sequence can be manually changed by stacking the dose setting elements in the stack.

In a possible embodiment, an outer dimension of the dose setting elements corresponds to an inner dimension of the container. This allows to take care of a high degree of precision in the delivery wherein the dose setting elements are moved inside the container along the inner wall of the container until the piston is engaged with the rear end of the container.

To engage the piston with the rear end of the container an outer dimension of the piston is greater than an inner dimension of the container. Furthermore, at least one of the dose setting elements is positioned in the initial position between the piston and a bung sealing the open rear end of the container. For the drug delivery the piston is moved from the piston loading position to the piston initial position in such a way that the piston and the dose setting elements in the initial position approach each other. Afterwards the piston and the dose setting elements are moved together from their initial position to their delivery position until the piston engaged the rear end of the container. Such limitation of the delivery movement of the piston ensures that the risk of delivery a failed dose is small.

In a further embodiment, all dose setting elements positioned in the initial position Seta fixed total dose volume by their number and their height. In more detail, each of the dose setting elements positioned in the stack position sets an individual sub-dose volume by their individual height or sets a same sub-dose volume by their same height. These allow a single device assembly line which can be switched relatively quickly and easily between different dose volumes and/or dose numbers.

A simple drug delivery device assembly comprises a storage stack positioned alongside the container, wherein a pre-determined number of dose setting elements is arranged in the storage stack. Therefore, the device assembly can be pre-filled with a pre-determined dose volume for each delivery process and/or with a pre-determined number of doses in a pre-determined order of the dose setting elements with the same dose volume and/or with different dose volumes.

In a further embodiment, a storage stack is positioned alongside the container, wherein dose setting elements with individual heights are arranged in the storage stack in pre-determined order. These allow modifying the dose volumes for each delivery process by changing the height of the dose setting elements and/or the dose numbers.

To set the dose setting elements to their initial position a loading lever is movable between a lever idle position and a lever loading position for transferring one of the dose setting elements from the stack position to the initial position.

The dose setting mechanism can easily be complemented with a dose counter coupled to a counter display. E.g. each sliding of one of the dose setting elements into the initial position is counted. In the counter display the number of the remaining doses to be delivered or the number of the doses already delivered is shown. The counter display may indicate a small number of remaining doses in another colour, e.g. in red, as a reminder.

In summary, the advantage of the invention is that the dose setting mechanism and a drug delivery device with such a dose setting mechanism is very easy and simple to use, even for weak patients and children. The dose setting mechanism in a drug delivery device require only a minimum of operating steps while exhibiting a high degree of precision in setting dose numbers with fixed dose volumes and in individual delivery of the set dose volume. The drug delivery device is preferably a pebble shape device and moves away from a usual pen architecture, where the mechanism is all in a line.

BRIEF DESCRIPTION OF THE DRAWINGS

The invention will now be described in further detail with reference to the drawings, in which.

DETAILED DESCRIPTION OF THE INVENTION

Figure 1:
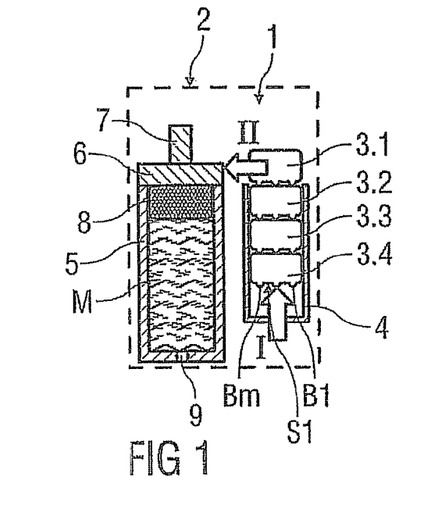
FIG. 1 to FIG. 5 illustrate a dose setting mechanism to a general embodiment of the invention.

FIG. 1 discloses a dose setting mechanism 1 for a drug delivery mechanism 2.

The dose setting mechanism 1 comprises a number of separate dose setting elements 3.1 to 3.n. The dose setting elements 3.1 to 3.n are stacked in a storage stack 4, e.g. in a cylindrical box or a vial, with an open top.

The dose setting elements 3.1 to 3.n are discs with a pre-determined height h. In FIG. 1 all discs have the same height h. Each of the dose setting elements 3.1 to 3.n positioned in the stack 4 sets an individual sub-dose volume by their height h or sets an equal sub-dose volume by their same height h. The discs are made from a hard material, e.g. plastic, glass or metal, which protects against shrinkage, warping and uneven surfaces. In order to slide easily the dose setting elements 3.1 to 3.n comprise a plurality of bulges B1 to Bm on at least one surface side S1, e.g. the bottom surface side. In a preferred embodiment, each dose setting element 3.1 to 3.n comprises three bulges B1 to B3 on the bottom side to slide with low friction. The bulges B1 to Bm also prevent the thickness D from being altered by humidity between the dose setting elements 3.1 to 3.n.

The drug delivery mechanism 2, e.g. an injector, a syringe or an inhalator, comprises a medical container 5 pre-filled with a total volume of a medicament M and a piston 6 with a piston rod 7. The piston 6 can be manually or automatically driven. The driver is not shown. The piston 6 is positioned above a rear end of the container 5. This rear end is opened and sealed by a bung 8. Moreover, the outer dimension of the piston 6 is greater than the inner dimension of the container 5, so that the piston 6 engages the rear end of the container 5. The stack 4 with the dose setting elements 3.1 to 3.n is arranged alongside the container 5.

For delivery of the medicament M the container 5 comprises on the opposite end to the rear end (so called front end) an opening 9. The opening 9 is differently dimensioned and designed depending on the kind of drug delivery mechanism 2 and/or kind of medicament M to be delivered. The opening 9 can be designed in a way that a needle and/or a needle adapter can be arranged at the front end. Alternatively, the opening 9 is just opened to realize a needle-less drug delivery device 2 (shown in FIG. 1). Furthermore, the stacked dose setting elements 3.1 to 3.n may be moved translationally up from a stack position I and to the left in an initial position II above the rear end of the container 5 between the piston 6 and the bung 8. For this purpose of separately transferring of the dose setting elements 3.1 to 3.n, transfer means are arranged which are not shown in FIG. 1.

For setting individual dose numbers a pre-determined number of the dose setting elements 3.1 to 3.n can be provided in the stack 4 during manufacturing of the drug delivery device 2 and/or before the drug delivery, e.g. before the injection or inhalation. For setting individual dose volumes for each dose the dose setting elements 3.1 to 3.n comprise a different height h. According to the embodiment of FIG. 1 the dose volumes of each dose (e.g. five doses) are the same in that the dose setting elements 3.1 to 3.n have the same height h. The height h of each dose setting element 3.1 to 3.n equals a sum of the thickness D of the individual dose setting element 3.1 to 3.n and the bulge height B1 (see FIG. 8).

Figure 2:
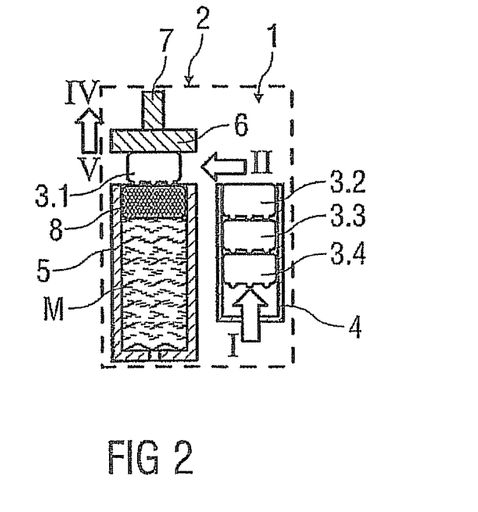

A possible embodiment of the drug delivery process is described successive by FIGS. 2 to 5. In FIG. 2 only one dose setting element 3.1 is set in the initial position II. For loading the dose setting element 3.1 in the initial position II the piston 5 may move translationally up in a piston loading position IV by a driver (not shown). The dose setting element 3.1 removes from his stack position I to the initial position II while the piston 6 is positioned in the piston loading position IV. After a pre-determined number of dose setting elements 3.1 to 3.n are transferred in their initial position II the piston 6 moves down in a piston initial position V in which the piston 5 is engaged with the last dose setting element 3.1 to 3.n in its initial position II. In the case that all dose setting elements 3.1 to 3.n are positioned in the initial position II they set a fixed total dose volume by their number and their height h.

Figure 3:
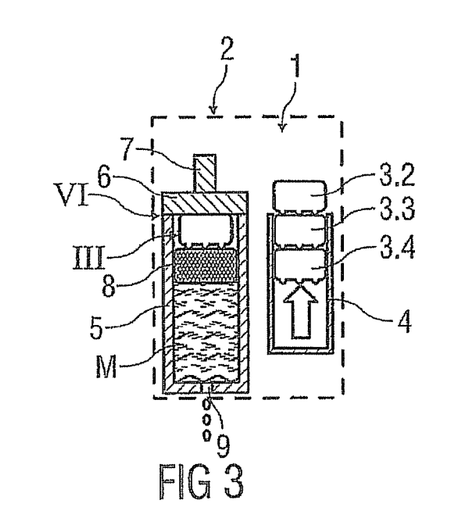

During the drug delivery the dose setting elements 3.1 to 3.n in the initial position II (in FIGS. 2 to 3 only one dose setting element 3.1) may translationally move down into the container 5 in a delivery position III shown in FIG. 3 by driving the piston 6 downwards from the piston loading position IV to the piston delivery position VI. Because the outer dimension of the dose setting elements 3.1 to 3.n corresponds to the inner dimension of the container 5 the dose setting elements 3.1 to 3.n in the initial position II may move inside the container 5 in a delivery position III at the end of the drug delivery. The movement of the piston 6 is limited by the individual height h and the number of the respective dose setting elements 3.1 to 3.n in the initial position II and by engaging the rear end of the container 5 (shown in FIG. 3). With other words: The total height of all dose setting elements 3.1 to 3.n in the initial position II corresponds to the length of the applying travel.

Figure 4:
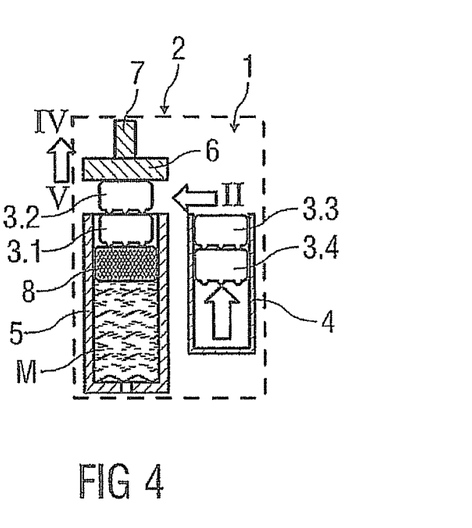

FIG. 4 shows setting a second dose by transferring the dose setting element 3.2 from the stack position I via the initial position II to the delivery position III.

Figure 5:
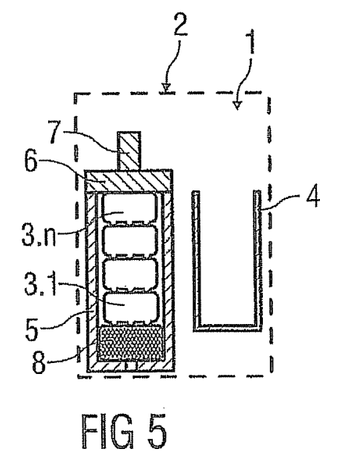

FIG. 5 shows the and of delivery with a delivery of a total dose volume and a pre-determined dose numbers of five by five arranged dose setting elements 3.1 to 3.5 in the delivery position III. At the end of delivery the piston 6 is engaged with the rear end of the container 5 in the piston delivery position VI (see FIG. 3 or 5).

Figure 6:
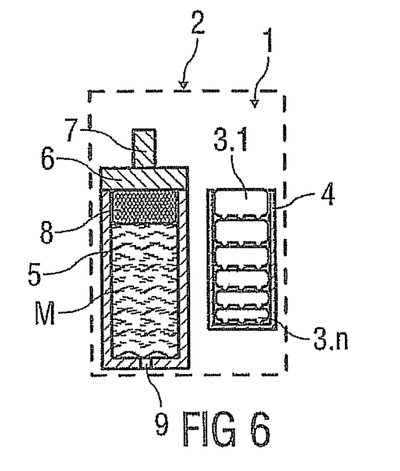
FIG. 6 illustrates alternative embodiment of the dose setting mechanism with different kinds of dose setting elements.
Figure 7:
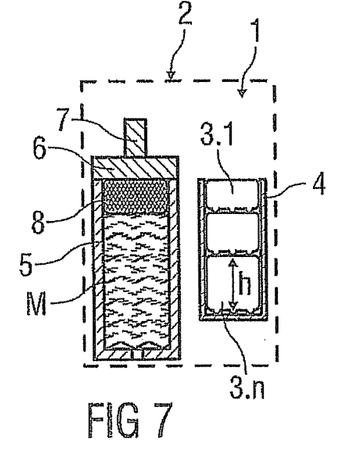
FIG. 7 illustrates a further alternative embodiment of the dose setting mechanism with further different kinds of dose setting elements.

FIGS. 6, 7 show different embodiments of the invention with a drug delivery device 2 with different dose volumes and/or individual dose numbers with individual dose volumes for a drug delivery.

In FIG. 6 the respective height h, especially the thickness D of the shown six dose setting elements 3.1 to 3.n in the stack position I increases from the bottom to the top so that a drug delivery with six decreasing doses is provided. The bulges B1 to Bm are all the same height h1.

In FIG. 7 the respective height h, especially the thickness D of the shown three dose setting elements 3.1 to 3.n in the stack position I decreases from the bottom to the top so that a drug delivery with three increasing doses is provided. The bulges B1 to Bm are exhibit all the same height h1.

Other embodiments with individual dose volumes and/or dose numbers are possible.

Figure 8:
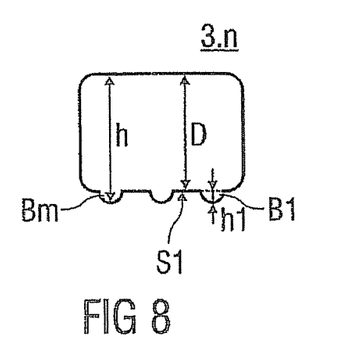
FIG. 8 illustrates an embodiment of a dose setting element.

FIG. 8 shows one possible embodiment of one dose setting element 3.n with a given thickness D and three bulges B1 to Bm on the bottom surface side S1. To easily slide the dose setting element 3.n the opposite ends are round and/or tapered. The height h of the dose setting element 3.n equals the sum of the thickness D and the bulge height h1, wherein the bulge height h1 of all bulges B1 to Bm are equal. The addition of bumps or bulges B1 to Bm makes the overall height dimension of the dose setting element 3.1 to 3.n easier to control during manufacture, since the bulges B1 to Bm will help to mitigate against any possible warping of the disc or dose setting element 3.1 to 3.n during manufacture and sliding. A further advantage of the bulges B1 to Bm is that it will minimise friction/stiction between the dose setting elements 3.1 to 3.n and make the disc loading mechanism easier to operate.

In the following, the mechanism principle and the use of the dose setting mechanism 1 according to the invention in a possible embodiment of a drug delivery device 2 is described in more detail.

The invention described in this form is a metering or dose setting mechanism 1 for advancing the piston 6 along the medication container 5 in order to cause a dose of medication M to be dispensed. The dose setting mechanism 1 is intended for use with a medication container 5 that consists of a container body and a piston 6 and/or bung 8 that moves along the body as the medication M is dispensed from the container 5. This includes a pre-filled cartridge as it is common in many injection devices as well as pre-filled syringes.

The operating principle of the proposed mechanism is that the dose setting device 1 contains the storage stack 4 of dose setting elements 3.1 to 3.n, also called "discs". The discs can in fact be of any shape to suit the medication container 5. Cylindrical containers 5 and/or storage stack 4 may be best served by circular discs. The height h of the discs is designed to be equal to the displacement of the medication container 5 and/or bung 8 required to dispense the desired "fixed" dose. Alternatively, the discs may be of varying height h, especially varying thickness D to deliver a sequence of different predetermined doses, for example, a dose that gradually increases as doses are taken from the dose setting device 1.

The dose setting device 1 contains the reciprocating piston 6 positioned directly above the open (non-dispensing) end of the medication container 5. Initially, this piston 6 is in contact with the bung 8 of the medication container 5, see FIG. 1, 6 or 7. To prepare a dose the piston 6 must first move away from the bung 8 into a piston loading position IV. A disc (=dose setting element 3.1 to 3.n) is then transferred from the storage stack 4 into the initial position II between the medication container 4/bung 8 and the piston 6, see FIG. 2 or 4. When the piston 6 is returned or moved to its original "dispense" position (=piston delivery position VI) the medication container bung 8 is displaced by a distance equal to the height h of the transferred dose setting element 3.1, see FIG. 3 or 5. The storage stack 4 of dose setting elements 3.1 to 3.n is moved upwards so that the next dose setting element 3.1 to 3.n is ready to be transferred. This could be accomplished by a spring acting on the bottom of the storage stack 4 or a screw thread device or a ratcheted piston device. Injection may be triggered by a mechanical skin sensor, e.g. a needle sleeve 17 (see FIG. 9).

To prepare a second dose the piston 6 is again moved to the piston loading position IV and a second dose setting element 3.2 is transferred from the storage stack 4 into the initial position II between the piston 6 and the previously transferred disc or dose setting element 3.1, see FIG. 4.

When the piston 6 is returned or moved to the piston delivery position VI the second dose is then dispensed. Subsequent doses are dispensed in the same manner. Once the dose setting elements 3.1 to 3.n are transferred from the storage stack 4 into the delivery position III they will form a second stack that will gradually move downwards into the medication container 5 as further dose setting elements 3.1 to 3.n are added to the top of the stack. When all doses have been delivered all dose setting elements 3.1 to 3.n will have been transferred from the storage stack 4 to the medication container 5, see FIG. 5.

In summary, a device design concept has been proposed that incorporates the dose setting mechanism 1 (also disc metering mechanism called). The basic concept design illustrates in FIGS. 9, 10, e.g. the basic components of the mechanism, the proposed overall size and shape of the external design and the proposed user interface. However, no detailed design of the sub-mechanisms, for example disc transfer mechanism and trigger mechanism, is shown in an abstract manner. E.g. the trigger mechanism may be connected to the needle cover 17. Once the needle cover 17 has been pushed back into the device the injection can be released.

Figure 9:
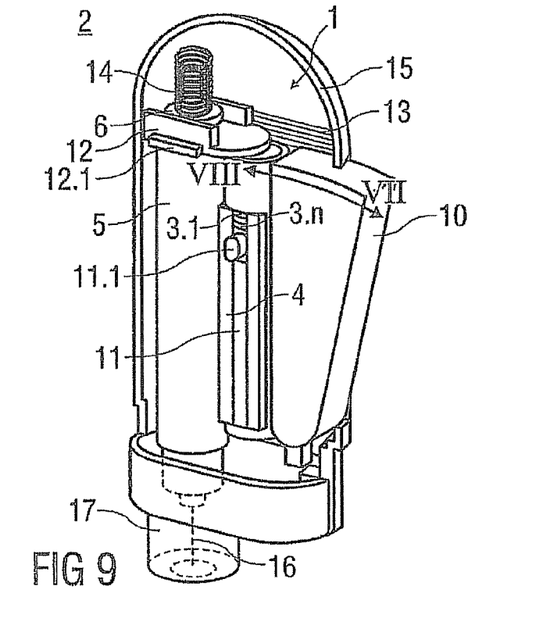
FIG. 9 illustrates the use of a dose setting mechanism according to the invention in a possible embodiment of a drug delivery device.

In FIG. 9 a possible embodiment of a drug delivery device 2 for administering a product is shown. The drug delivery device 2 comprises the dose setting mechanism 1 arranged alongside the medical container 5. The medical container 5 and the dose setting mechanism 1 may be fixed in a housing 15. To transfer each dose setting element 3.1 to 3.n separately, transfer means are arranged above the rear end of the container 5 and alongside the storage stack 4. The transfer means comprises in a possible embodiment a slide rail 12 arranged above the rear end of the container 5 and a loading lever 10 arranged alongside the storage stack 4. The transfer means, also called disc loading mechanism, are operated by the loading lever designed as e.g. a side action button, which is comfortable for patients with reduced manual dexterity. Patients have the option of performing this action by using the fingers, thumb, entire hand, or even pushing the device against a fixed surface such as a table or wall.

To fix the already transferred and in the initial position arranged dose setting elements 3.1 to 3.n the slide rail 12 comprise a tongue 12.1 latching respectively in grooves 13 on inner wall of the housing 15.

Figure 10:
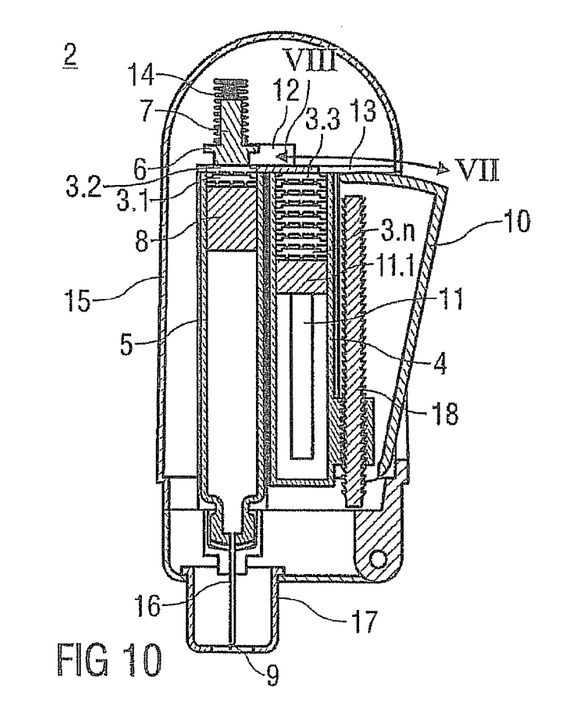
FIG. 10 illustrates a longitudinal section of the dose setting mechanism according to FIG. 9, FIG. 11 to FIG. 13 illustrate a dose setting mechanism according to a another embodiment of the invention.

The loading lever 10 is shown in detail in FIG. 10. There is shown only one embodiment, other embodiments of triggering are possible.

To set the dose setting elements 3.1 to 3.n to their initial position II the loading lever 10 is moveable, e.g. pivoted, between a lever idle position VII and a lever loading position VIII for transferring one of the dose setting elements 3.1 to 3.n from their stack position I to their initial position II. The loading lever 10 is formed in one possible embodiment as a pivot push button arranged partly outside the housing 15 and pivoted in the housing 15.

To set the next dose setting element 3.1 to 3.n different setting elements may be provided. In the embodiment according to FIG. 9 the storage stack 4 has a longitudinal slot 11, in which an arm 11.1 is moveable. To fix the arm 11.1 in a given position the inner wall of the housing 15 comprises a number of corresponding grooves 13. The grooves 13 may be different and correspond with the arm 11.1 and/or the tongue 12.1. The arm 11.1 is arranged in that way that its end protrudes from the housing 15. The arm 11.1 may be slid into the next position in a different manner, e.g. by a screw element 18 or by a spring. Alternatively, the dose setting mechanism 1 is typically a screw thread device and/or ratcheted piston device. Screw thread devices will typically have a tolerance chain for the displacement of a single dose that runs through several components.

When the dose setting elements 3.1 to 3.*n* are transferred to their initial position II the piston 6 moves into its piston loading position IV. The piston 6 is a reciprocating piston positioned above the rear end of the container 5 and moveable between the piston initial position V and the piston loading position IV during the loading process and between the piston initial position V and the piston delivery position VI during drug delivery. To fix the piston 6 in its piston initial position V before drug delivery an actuating element 14, e.g. a spring, is arranged above the transfer means 12.

The container 5 may be pre-filled with a total volume of the medicament M or may be a pre-filled syringe. All dose setting elements 3.1 to 3.*n* positioned in the initial position II Seta fixed total dose volume by their number and their height h for a single dose. All dose setting elements 3.1 to 3.*n* in the storage stack 4 set a fixed total dose volume by their total number and their total height for all doses to be delivered. Each of the dose setting elements 3.1 to 3.*n* positioned in the stack position I sets an individual sub-dose volume by their individual height h or sets an equal sub-dose volume by their same height h.

The described dose setting mechanism 1 can be used in a drug delivery device 2 designed as a fixed-dose injection device, either manually operated or automatically operated as an auto-injector (i.e. the delivery piston moves with the release of some form of stored energy, e.g. energy is provided by pushing the loading lever 10 against a spring (not shown) inside the housing 15). The drug delivery device 2 can be used as a system with a usual needle 16 and usual needle shield 17 (shown in FIGS. 8, 9) or needle-less (shown in FIGS. 1 to 7).

The dose setting mechanism 1 appears to be best suited for disposable devices rather than re-usable devices (where the medication container and/or the dose setting mechanism can be removed and replaced) owing to the complicated nature of resetting the disc mechanism. There are a number of drug therapies, delivered by means of injection, which require a number of fixed doses to be administered (rather than a user-selected variable dose as required by diabetics being treated with insulin). These treatments include migraine. GLP-1 for diabetes, anti-coagulants, hormone therapy or other non-medical usage, e.g. for adhesive injection, etc.

This disc metering mechanism and/or dose setting mechanism 1 can also be used to deliver a variable (non-patient selectable) fixed dose. These doses may be pre-determined during the specification and manufacture of the drug delivery device 2. For example, the dose setting mechanism 1 may automatically deliver a titration regime where the "fixed" dose gradually increases over the life of the drug delivery device 2. The dose setting mechanism 1 may also deliver seven fixed doses for one week of treatment followed by seven injections of a second, larger, fixed dose for the following week. This can be accomplished simply by selecting discs or dose setting elements 3.1 to 3.*n* of the appropriate thickness or height h and loading them in the correct order into the storage stack 4.

The injection moulding tolerance could be further improved by adding bumps to one of the "disc-contacting" surfaces of the dose setting element 3.1 to 3.*n*. The critical dimension would then be the total disc thickness or height including the height of the bump. Three bumps is probably the optimum number as it is the minimum number of bumps that provides a stable stack of discs or dose setting elements 3.1 to 3.*n*.

A further advantage of the drug delivery device 2 is that it should be very easy to make a platform device from the dose metering mechanism or dose setting mechanism 1.

Different dose volumes or sizes and/or the number of doses can be modified simply by changing the height h, especially the thickness D of the dose setting elements 3.1 to 3.*n* in the storage stack 4. For example, if the drug delivery device 2 accommodates a medication container 5 capable of delivering 2.8 ml of medication M over a 42 mm bung displacement then the dose setting mechanism 1 could be designed to work with discs or dose setting elements 3.1 to 3.*n* of 1.5 mm (28 doses×0.1 ml), 3 mm (14 doses×0.2 ml), 6 mm (7 doses×0.4 ml) etc. Therefore, a single drug delivery device 2 with the above described dose setting mechanism 1 could be switched relatively quickly/easily between different dose volumes/sizes and/or number of doses.

In an additional embodiment (not shown), the dose setting mechanism may be complemented with a dose counter coupled to a counter display. The dose counter counters e.g. each sliding of one of the dose setting elements into the initial position. In the counter display the number of the remaining doses to be delivered or the number of the doses already delivered may be shown. Preferably, the counter display may indicate a small number of remaining doses in another colour, e.g. in red, as a reminder.

Many existing injection devices take the form of a pen shape. This may be due to the fact that the primary package, either cartridges or pre-filled syringes are based on the shape of syringes. Also, the piston rod of the injection device tends to be as long as the primary package itself and typically needs to be placed in line with the primary package adding to the elongated pen shape of the device. This can cause problems for the user because the actuation button is often at the non-needle end of the device and can require considerable thumb extension to operate. This can be a problem for patients who suffer from reduced manual dexterity, e.g. a large number of diabetes patients or elderly patients. The proposed mechanism does not feature a fixed piston rod and the storage stack 4 of discs can be assembled alongside the primary package, e.g. the container 5. Therefore, the overall shape of the device is not constrained to a pen shape. This mechanism has been designed to fit inside a much shorter device that will fit comfortably in a patient's hand.

Figure 11:
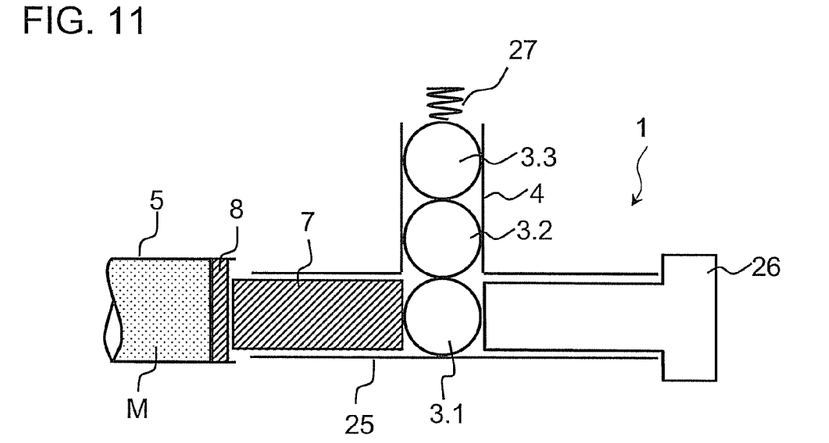
Figure 12:
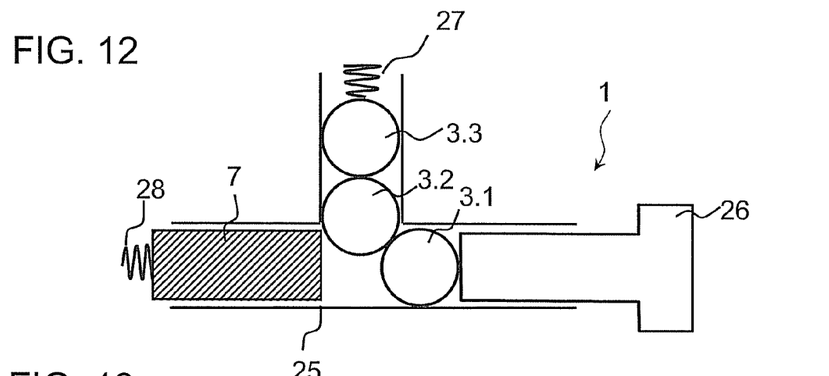
Figure 13:
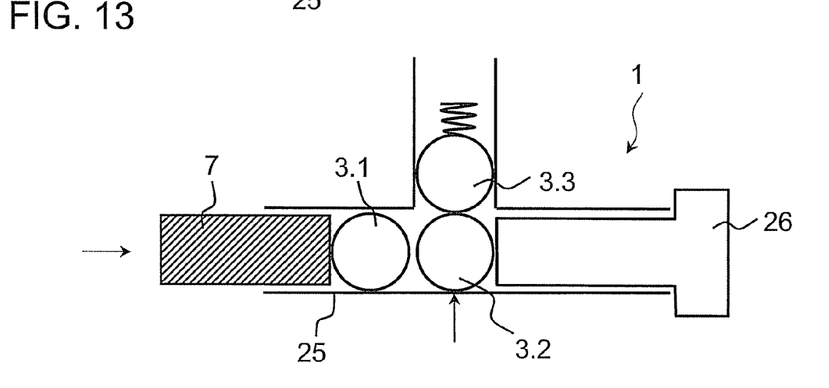

In an alternative embodiment, which is shown in FIGS. 11 to 13, the dose setting mechanism 1 comprises a main chamber 25 and storage stack 4 which are connected by a branch connection may be formed as a T piece. The main chamber 25 is cylindrically shaped and has a distal opening and a proximal opening. The storage stack 4 is cylindrically shaped. The storage stack 4 is suitable for holding a multitude of dose setting elements 3.1, 3.2, 3.3. A piston rod 7, which is located at least partly in the distal part of the main chamber 25, and a button 26, which is located at least partly in the proximal part of the main chamber 25, are moveable along the main axis which is the longitudinal axis of the main chamber 25. The piston rod 7 is configured to push a bung 8 along an inside wall of a container 5 which contains the drug M so that the drug is delivered.

The dose setting elements 3.1, 3.2, 3.3 are formed as balls. In this embodiment a first, a second and a third dose setting element 3.1, 3.2, 3.3 are shown. In a first position, which is shown in FIG. 11, the first dose setting element 3.1 is located in the main chamber 25 between the button 26 and the piston rod 7. The other dose setting elements 3.2, 3.3 are located in the storage stack 4. A spring 27 which may be located at the end of the storage stack 4 impacts a spring force to the dose setting elements 3.1, 3.2, 3.3, the direction of the spring force being orthogonal to the main axis of the main chamber 25.

During dose setting the button 26 is moved to the proximal direction with respect to the main chamber 25, as shown in FIG. 12. The spring force pushes the second dose setting element 3.2 into the main chamber 25. To avoid perfect alignment of the dose setting elements 3.1, 3.2, 3.3 with an axis orthogonal to the main axis of the main chamber 25 a small force may impact to the first dose setting element 3.1, which is located in the main chamber 25. A spring 28 which is located at the distal and of the piston rod 7 may cause this force. The spring 28 may be located between the distal end of the piston rod 7 and the bung 8 (not shown in FIG. 12) or between the distal end of the piston rod 7 and a part of the housing (not shown in FIG. 12). The force causes slight movement of the piston rod 7 and the first dose setting element 3.1 to the proximal direction which ensures that the first and second dose setting elements 3.1, 3.2 are misaligned so that the second dose setting element 3.2 pushes the first dose setting element 3.1 into the proximal direction. The second dose setting element 3.2 moves into the space left by the proximal movement of the button 26. The dose is set when the first and second dose setting element 3.1, 3.2 are located in the main chamber 25. The force impacted by the springs 27, 28 may be balanced to achieve the above-mentioned effect. The main chamber 25 may be shaped to ensure that the centre of the dose setting element, which has moved to the main chamber 25, is slightly offset to the main axis of the main chamber 25. Radial forces may maintain returning of this dose setting element to the storage stack 4.

The dose is delivered when the button 26 is moved to the distal direction, thereby pushing the first dose setting element 3.1, the second dose setting element 3.2 and the piston rod 7 to the distal direction which causes distal movement of the bung 8 so that the drug is delivered. FIG. 13 illustrates the state after delivery. A further dose may be set by moving the button 26 to the proximal direction so that the third dose setting element 3.3 moves to the main chamber 25. An alternative embodiment may have more than three dose setting elements, so that the embodiment is configured to set and deliver more than three doses. The accuracy of dose setting and delivery may be improved in comparison with a conventional drug delivery device due to the high precision of the balls serving as dose setting elements and their lack of elasticity.

The drug delivery device is reset by returning the dose setting elements to the storage stack 4. A resetting mechanism (not shown in FIG. 13) is provided, the resetting mechanism being configured to push the dose setting element 3.2 which is located adjacent to storage stack 4 off the main axis of the main chamber 25 so that the dose setting element 3.2 moves into the storage stack 4. The piston rod 7 moves to the proximal direction when the dose setting elements, except the first one 3.1, are moved into the storage stack 4. The resetting mechanism may be embodied as arm or lever configured to move radially into the main chamber 25, thereby pushing the dose setting element 3.2 into the storage stack 4.

Figure 14:
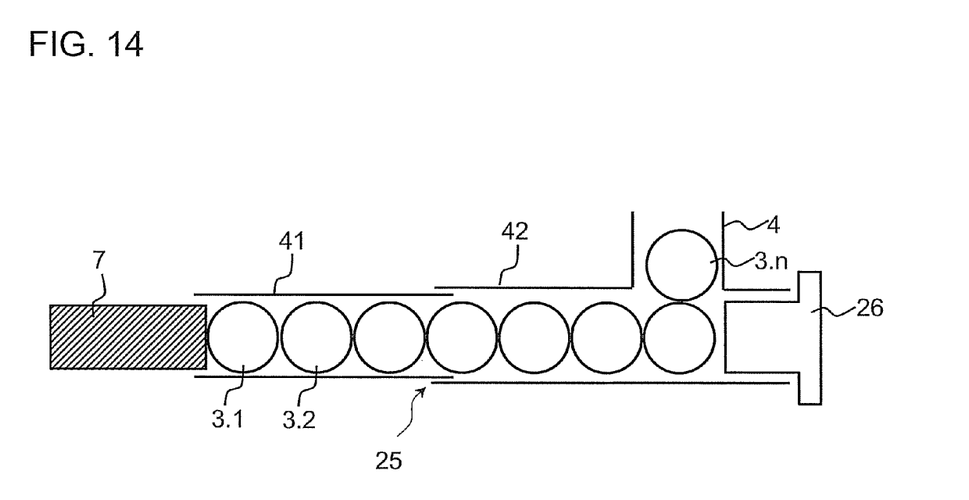
FIG. 14 illustrates a dose setting mechanism according to a further embodiment of the invention.

FIG. 14 shows an embodiment of a dose setting mechanism having an extendable main chamber 25. The collapsible nature of the stack of dose setting elements allows that the piston rod 7 travels along the extendable main chamber 25. The main chamber 25 comprises telescope elements 41, 42. A first cylindrically shaped telescope 41 element may be arranged inside a second cylindrically shaped telescope element 42 at an initial state (not shown in FIG. 14). The second telescope element 42 is configured to extend so that the length of the main chamber 25 is increased. The main chamber 25 extends with increasing number of dose setting elements 3.1 ... 3.n which are moved to the main chamber 25. Thus the piston rod travel is e.g. twice as large as the length of the device.

The mechanism could be utilized in a number of different drug delivery devices, but is likely to be most useful in devices that require dispensing accurate volumes liquid medication. This will include injection, whether with a needle or needle-free device, and inhalation, including nasal and buccal sprays. It shall be mentioned that the features of the embodiments may be combined.

LIST OF REFERENCES

1 Dose setting mechanism
2 Drug delivery device
3.1 to 3.n Dose setting elements
4 Storage stack
5 Container
6 Piston
7 Piston rod
8 Bung
9 Opening
10 Loading lever
11 Slot
11.1 Arm
12 Slide rail
12.1 Tongue
13 Grooves
14 Activating element
15 Housing
16 Needle
17 Needle shield
25 Main chamber
26 Button
27, 28 Spring
41, 42 Telescope element
B1 to Bm Bulges
D Thickness of dose setting element
h Height of dose setting element
h1 Bulge height
S1 Surface Side
I Stack position
II Initial position
III Delivery position
IV Piston loading position
V Piston initial position
VI Piston dispense position
VII Lever idle position
VIII Lever loading position

The invention claimed is:

1. Dose setting mechanism for a drug delivery device, comprising a plurality of separate stacked dose setting elements stacked in a storage stack, wherein a dose volume and/or a dose number are/is set by moving at least one of the respective dose setting elements from a stack position in the storage stack translationally up to an initial position outside of the storage stack, and
  wherein a medicament dose volume is applied by moving at least one dose setting element from the initial position to a dispense position and
  wherein the movement of the dose setting element from the initial position to the dispense position is limited by at least a height of the dose setting element in the initial position,
  wherein each dose setting element comprises a plurality of bulges on at least one surface side,
  wherein the height of each dose setting element equals a sum of the thickness of the dose setting element and the bulge height.

2. Dose setting mechanism for a drug delivery device, comprising
   a plurality of separate stacked dose setting elements, wherein a dose volume and/or a dose number are/is set by moving at least one of the respective dose setting elements from a stack position to an initial position, and
   wherein a medicament dose volume is applied by moving at least one dose setting element from the initial position to a dispense position and
   wherein the movement of the dose setting element from the initial position to the dispense position is limited by at least a height of the dose setting element in the initial position,
   wherein each dose setting element is formed as a ball.

3. Dose setting mechanism according to claim 1, wherein the individual height of the respective dose setting element positioned in the initial position defines an applying travel for one dose.

4. Dose setting mechanism according to claim 1, wherein the individual height of the respective dose setting element positioned in the initial position defines the dose volume of the medicament for one dose to be delivered.

5. Dose setting mechanism according to claim 1, wherein the number of the respective dose setting elements positioned in the stack position defines the dose number to be separately delivered.

6. Dose setting mechanism according to claim 1, wherein the dose setting elements have the same height or different heights to define the same or different dose volume of the medicament to be separately delivered.

7. Dose setting mechanism according to claim 1, wherein the respective bulge heights of all bulges of a respective dose setting element are equal.

8. Dose setting mechanism according to claim 1, wherein the respective bulge heights of all bulges of all dose setting elements are equal and the thicknesses of the dose setting elements vary.

9. Dose setting mechanism according to claim 1, wherein the respective dose setting element comprises a disc.

10. Dose setting mechanism according to claim 1, wherein the respective dose setting elements are moveable backwards from the dispense position via the initial position to the stack position.

11. Drug delivery device for administering a product, comprising
   a dose setting mechanism according to claim 1,
   a medical container with a total volume of a medicament,
   a reciprocating piston with a piston rod positioned above a rear end of the container and moveable between a piston loading position and a delivery position,
   transfer means transferring at least one of the dose setting elements of the dose setting mechanism from a stack position to an initial position above said rear end of said container while the piston is positioned to the loading position,
   characterized in that each dose setting element comprises a plurality of bulges on at least one surface side,
   wherein the height of each dose setting element equals a sum of the thickness of the dose setting element and the bulge height.

12. Drug delivery device according to claim 11, wherein an outer dimension of said dose setting elements corresponds to an inner dimension of the container.

13. Drug delivery device according to claim 11, wherein an outer dimension of the piston is greater than an inner dimension of the container.

14. Drug delivery device according to claim 11, wherein at least one of the dose setting elements is positioned in the initial position between the piston and a bung sealing the open rear end of the container.

15. Drug delivery device according to claim 11, wherein all dose setting elements positioned in the stack position set a fixed total dose volume for a number of doses corresponding to the number of the dose setting elements.

16. Drug delivery device according to claim 11, wherein each of the dose setting elements positioned in the stack position sets an individual sub-dose volume by their individual height or sets an equal sub-dose volume by their same height.

17. Drug delivery device according to claim 11, wherein a storage stack is positioned alongside the container, wherein a pre-determined number of dose setting elements are arranged in the storage stack.

18. Drug delivery device according to claim 11, wherein a storage stack is positioned alongside the container, wherein a pre-determined number of dose setting elements with individual heights are arranged in the storage stack in pre-determined order.

19. Drug delivery device according to claim 11, wherein a loading lever is movable between a lever idle position and a lever loading position for transferring one of the dose setting elements from the stack position to the initial position.

* * * * *